United States Patent [19]
Hawk

[11] Patent Number: 6,086,587
[45] Date of Patent: Jul. 11, 2000

[54] MULTI-HEAD SUCTION ASSEMBLY FOR USE IN SURGICAL PROCEDURES

[76] Inventor: Rodney Hawk, 762 Dawes Dr., Yardley, Pa. 19067

[21] Appl. No.: 09/113,701

[22] Filed: Jul. 10, 1998

[51] Int. Cl.⁷ .................................................. A61B 17/56
[52] U.S. Cl. ............................................. 606/53; 604/902
[58] Field of Search ............................... 606/79; 604/902; 433/91, 93; 15/300.1

[56] References Cited

U.S. PATENT DOCUMENTS

| | | | |
|---|---|---|---|
| D. 270,960 | 10/1983 | Parise et al. | D32/21 |
| 3,623,483 | 11/1971 | Dyer, Jr. | 128/276 |
| 4,621,387 | 11/1986 | Noser | 15/167 |
| 5,116,165 | 5/1992 | Salyer | 407/54 |
| 5,203,653 | 4/1993 | Kudla | 408/207 |
| 5,358,507 | 10/1994 | Daily | 604/902 |
| 5,458,563 | 10/1995 | Stewart | 601/162 |
| 5,462,548 | 10/1995 | Pappas | 606/80 |
| 5,544,383 | 8/1996 | Gamble | 15/106 |
| 5,551,731 | 9/1996 | Gray et al. | 15/300.1 |
| 5,628,747 | 5/1997 | Richelsoph . | |
| 5,685,836 | 11/1997 | DiPerna | 604/19 |

*Primary Examiner*—Michael Buiz
*Assistant Examiner*—Jonathan D. Goldberg
*Attorney, Agent, or Firm*—LaMorte & Associates

[57] ABSTRACT

A suction assembly for use in a surgical procedure. The assembly includes a plurality of suction head attachments. Each of the suction head attachments has a base segment, a tip segment and a suction conduit that extends through the base segment and the tip segment. The base segment of each of the suction head attachments has a common configuration. However, the tip segment of each of the suction head attachments has a unique configuration. The assembly also includes a single handle element. A coupling mechanism is disposed at a first end of the handle element. The coupling mechanism is adapted to selectively engage the base segment of any of the plurality of suction head attachments. The handle element also connects to a suction source. As the handle element connects to one of the suction head attachments, the handle element interconnects the suction head attachment to the suction source.

16 Claims, 5 Drawing Sheets

MULTI-HEAD SUCTION ASSEMBLY FOR USE IN SURGICAL PROCEDURES

BACKGROUND OF THE INVENTION

1. Field of the Invention

In general, the present invention relates to suction devices used to evacuate and clean surgical sites within the body that are exposed during a surgical procedure. More particularly, the present invention relates to suction devices that are used during the different stages of a total hip arthroplasty procedure.

2. Description of the Prior Art

The medical field is replete with different types of suction devices that are used to evacuate and/or irrigate sections of the human body exposed during surgical procedures. Many of the suction instruments are generic in design and are used by surgeons in a wide variety of procedures. Such generic suction devices include Yankauer instruments, Poole instruments, Frazier instruments, sigmoidoscopic instruments and the like. Other suction devices are specifically designed for use in a single type of surgical procedure and have few applications outside of that surgical procedure.

The amount of suction required in a surgical procedure is directly proportional to the amount of blood and debris released within the surgical cavity by that surgical procedure. The removal of blood and debris from a surgical cavity is important in order to prevent the many different complications that may occur if the surgical cavity is not properly evacuated prior to the cavity being closed.

Few traditional operations create more debris during the coarse of the operation that does a total hip arthroplasty, wherein the hip joint is replaced. In the course of a traditional total hip arthroplasty, a femoral neck osteotomy is performed, wherein the neck of the femur is removed. A reamer is then used to ream the femoral canal to make space for the femoral prosthetic device. Likewise, the acetabular socket in the hip is reamed to make space for an acetabular cup. As the femoral canal and the acetabular socket are reamed, a great deal of debris is generated. The debris is a mixture of blood with large and small pieces of bone and bone marrow.

The reaming of the femoral canal and the acetabular socket are typically performed with dedicated reamers that are designed to remove as much material as is possible from the cavity being reamed. An example of a femoral canal reamer is shown in U.S. Pat. No. 5,628,747 to Richelsoph, entitled Device For Removing Cancellous Bone. Examples of acetabular socket reamers are shown by U.S. Pat. No. 5,116,165 to Salyer, entitled Acetabular Reamer Cup and U.S. Pat. No. 5,203,653 to Kudla, entitled Reamer For Shaping Bone Sockets.

Although dedicated prior art reaming devices for the femoral canal and the acetabular socket do remove much of the debris created by the reaming procedure, they do not remove all the debris. Consequently, prior to the placement of a prosthetic device into a reamed cavity, a surgeon will typically suction the reamed cavity. By sectioning the reamed cavity, the surgeon hopes to remove any small fragments of bone or other debris that my be detrimental to the patient if left in place. Although surgeons rely upon specialized instruments to ream the femoral canal and the acetabular socket, they typically do not use specialized instruments to clean the femoral canal and acetabular sockets after they have been reamed. Rather, surgeons commonly rely upon manual wiping and general purpose suction devices to complete the cleaning task.

As the femoral canal and acetabular socket are reamed, debris adheres to the walls of the reamed surfaces. Accordingly, to properly clean the reamed surfaces, the reamed surfaces must be wiped while the debris is being evacuated. The simultaneous wiping and suctioning of debris takes a significant portion of the surgeon's time and adds significantly to the length and cost of the surgical procedure.

The shape of a reamed femoral canal is very different from the shape of a reamed acetabular socket. Consequently, wiping implements and suction implements that are useful for the femoral canal are typically not proper for use within the acetabular socket. As a result, a surgeon must change implements and connect different suction devices to the suction source. This also adds to both the length and the cost of the surgical procedure.

A need therefore exists for a suction system that is specifically designed to assist a surgeon in a total hip arthroplasty, wherein the suction system more effectively cleans the surgical cavities and reduces the time required for the surgical procedure. This need is met by the present invention as described and claimed below.

SUMMARY OF THE INVENTION

The present invention is a suction assembly for use in a surgical procedure. The assembly includes a plurality of suction head attachments. Each of the suction head attachments has a base segment, a tip segment and a suction conduit that extends through the base segment and the tip segment. The base segment of each of the suction head attachments has a common configuration. However, the tip segment of each of the suction head attachments has a unique configuration.

The assembly also includes a single handle. A coupling mechanism is disposed at a first end of the handle element. The coupling mechanism is adapted to selectively engage the base segment of any of the plurality of suction head attachments. The handle element also connects to a suction source. As the handle element connects to one of the suction head attachments, the handle element interconnects that suction head attachment to the suction source.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE INVENTION

Although the present invention system can be used by a surgeon in many different types of surgery, such as in a shoulder joint replacement, the present invention system is especially well suited for use in a total hip replacement procedure. Accordingly, by way of example, the present invention system will be configured for use in a total hip arthroplasty in order so set forth the best mode contemplated for the invention.

Figure 1:
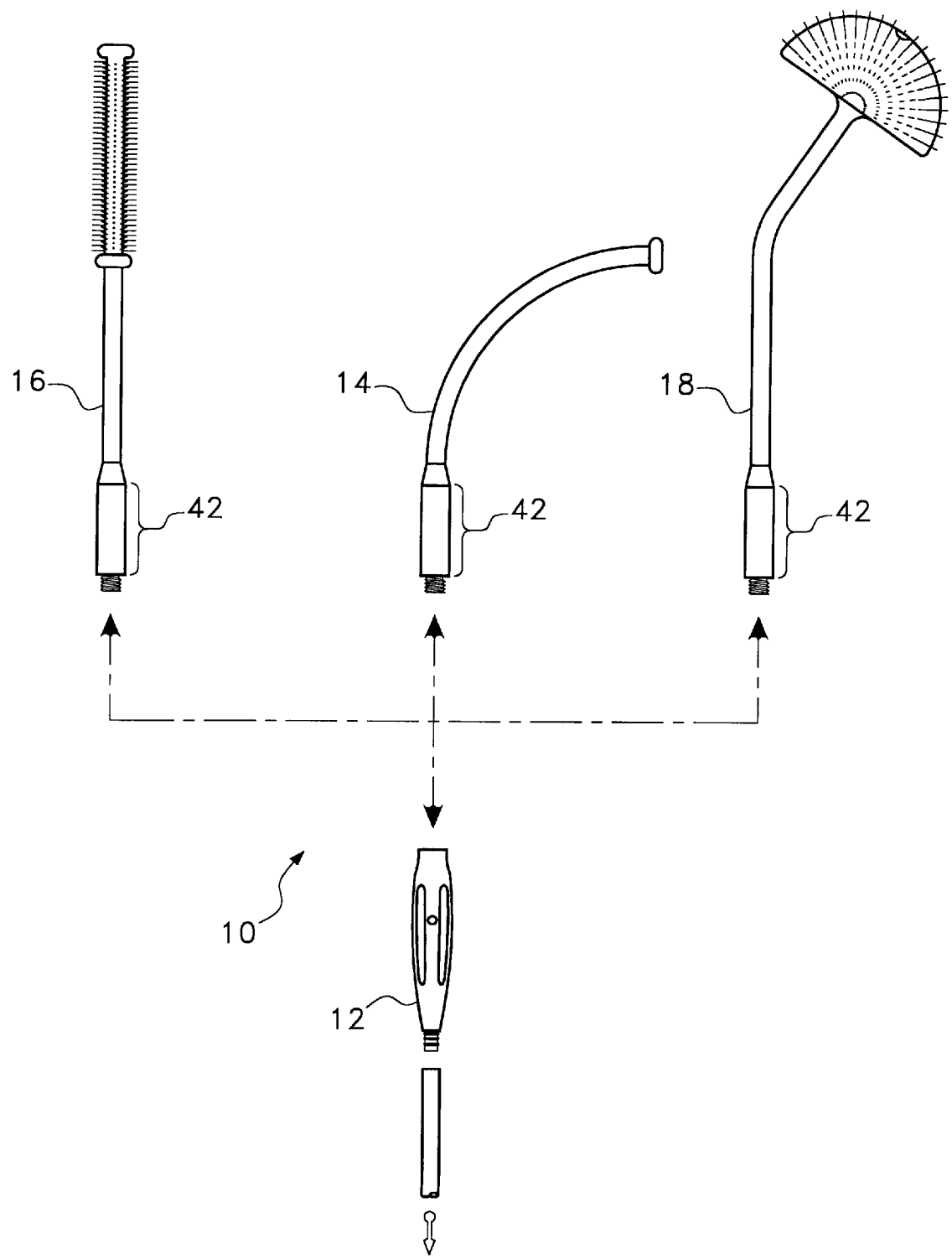
FIG. 1 is an exploded view of an exemplary embodiment of the present invention suction assembly containing three different suction head attachments.

Referring to FIG. 1, an exemplary embodiment of a suction assembly 10 is shown in accordance with the present invention. The suction assembly 10 is comprised of a handle element 12 and a plurality of specialized suction head attachments 14, 16, 18 that can be selectively attached to the handle element 12. As will later be explained, the various suction head attachments provided can be adapted to the needs of a specific surgical procedure. Accordingly, as a surgeon is performing that specific surgical procedure, the surgeon needs only to replace the suction head attachment on the handle element 12. Time is therefore not wasted on connecting different suction instruments to the operating room suction source at different points in the operation. The reduction is surgical time and surgical instruments significantly reduces the cost of the surgery and reduces the amount of time the patient is anaesthetized.

In the embodiment of FIG. 1, three separate suction head attachments 14, 16, 18 are shown. However, it will be understood that any number of different suction head attachments can be provided depending upon the surgical procedure being performed and the preferences of the surgeon. The embodiment of the suction assembly 10 set forth in FIG. 1 is designed for use in a total hip arthroplasty. The shown example contains an intermedullary brush suction head attachment 16, an acetabular brush suction head attachment 18 and at least one general purpose suction head attachment 14. In FIG. 1, the general purpose suction head attachment 14 shown has the general shape of a Yankauer instrument. However, depending upon the preferences of the surgeon, the general purpose suction head attachment 14 can be formed to simulate most any prior art suction device, such as a Poole instrument, a Frazier instrument, a sigmoidoscopic instrument or the like.

Figure 2:
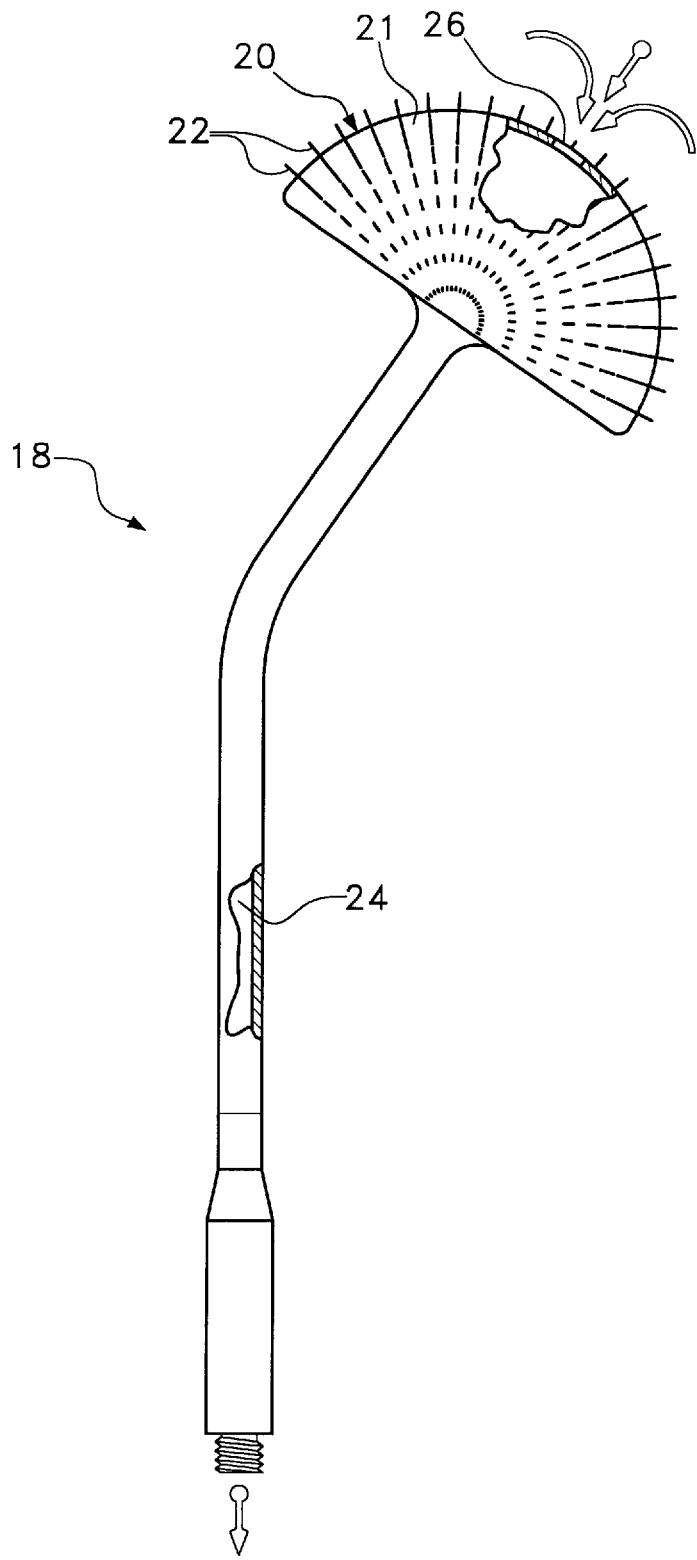
FIG. 2 is a fragmented side view of a first embodiment of an acetabular brush suction head attachment in accordance with the present invention.

Referring to FIG. 2, a first embodiment of an acetabular brush suction head attachment 18 is shown. The acetabular brush suction head attachment 18 is used by a surgeon in a total hip arthroplasty to clean the acetabular socket after the acetabular socket has been reamed and before a prosthetic acetabular cup is set into the socket. The acetabular brush suction head attachment 18 has a head section 20 that contains a generally hemispherically shaped surface 21. The radius of the generally hemispherically shaped surface 21 is preferably either equal to or smaller than the radius of the reamer used to ream the acetabular socket.

A plurality of bristles 22 radially extend from the generally hemispherically shaped surface 21 of the acetabular brush attachment 18. The bristles 22 are preferably plastic and are placed far enough apart to allow blood and bone debris to freely flow between bristle clusters. After the acetabular socket has been reamed on a total hip arthroplasty, the head section 20 of the acetabular brush attachment 18 is placed into the reamed socket. As the acetabular brush attachment 18 is moved, the bristles 22 move across the reamed surfaces of the acetabular socket and remove debris from the walls of the acetabular socket. Since the generally hemispherically shaped surface 21 of the head section 20 mimics the shape of the reamed acetabular socket, most every surface of the acetabular socket is contacted as the acetabular brush attachment 18 is moved across the acetabular socket. Consequently, the acetabular socket is cleaned in a very rapid and efficient manner.

A suction conduit 24 passes through the acetabular brush attachment 18. The suction conduit 24 extends into the head section 20 of the acetabular brush attachment 18. In the shown embodiment, a suction aperture 26 is present at the apex of the generally hemispherically shaped surface 21. The suction aperture communicates with the interior of the head section 20 and the suction conduit 24. As the generally hemispherically shaped surface 21 of the acetabular brush attachment 18 moves across the reamed acetabular socket, the debris loosened by the brush bristles are evacuated into the suction conduit 24, through the suction aperture 26. Provided the acetabular brush attachment 18 is adequately manipulated, the suction aperture 26 at the apex of the generally hemispherically shaped surface 21 will pass over most all surfaces of the reamed acetabular cavity. Consequently, all debris loosened by the bristles 22 is evacuated through the suction canal 24 and the reamed acetabular socket is rapidly and effectively cleaned.

Figure 3:
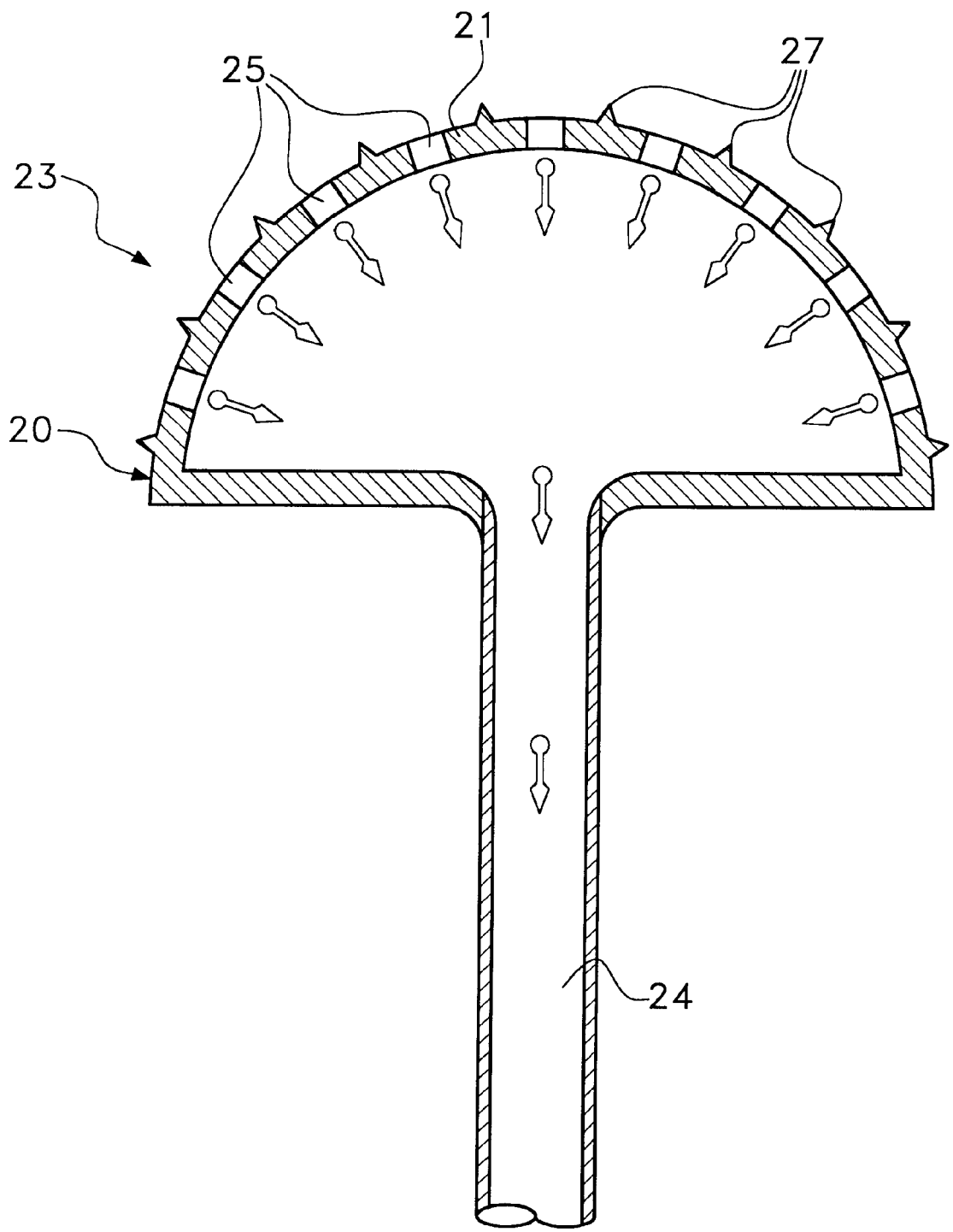
FIG. 3 is a fragmented cross-sectional view of a second embodiment of an acetabular brush suction head attachment in accordance with the present invention.

Referring to FIG. 3, an alternate embodiment of an acetabular brush 23 is shown. Features that are the same as the previous embodiment will be identified with the same reference numerals.

In the shown embodiment, a plurality of apertures 25 are disposed in the generally hemispherically shaped surface 21 of the head section. Each of the apertures 25 leads into the interior of the head section 20, which communicates with the suction conduit 24. As such, as the generally hemispherically shaped surface 21 of the head section 20 is brought into contact with a reamed acetabular socket, debris is suctioned into the interior of the suction head 20 through the various apertures 25. Once in the suction head, the debris is evacuated through the suction conduit 24.

The embodiment of FIG. 3 also differs from the embodiment of FIG. 2 in that the embodiment of FIG. 3 has flexible nubs 27 protruding from the exterior of the generally hemispherically shaped surface 21 rather than traditional brush bristles. The nubs 27 can be plastic, elastomeric or any other flexible protrusion. The purpose of illustrating the nubs 27 is to make it clear that the acetabular brush of the present invention can have any flexible protrusions extending from its exterior that are capable of freeing debris from the surfaces of the reamed acetabular socket.

Figure 4:
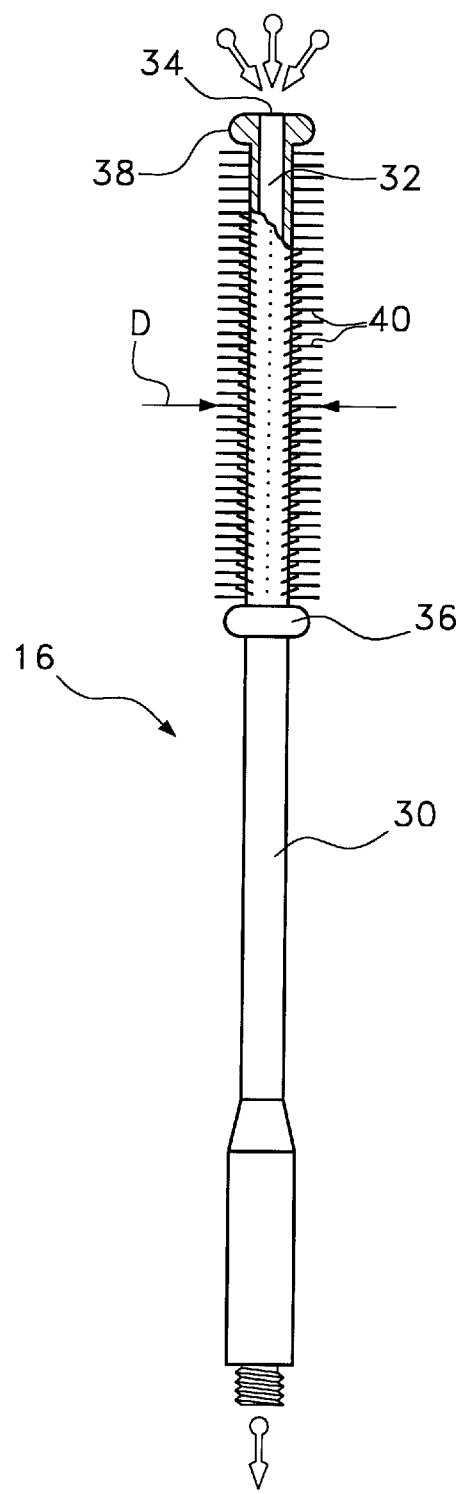
FIG. 4 is a fragmented side view of an intermedullary brush suction head attachment in accordance with the present invention.

Referring now to FIG. 4, a clearer view of the intermedullary brush attachment 16 is shown. In a total hip arthroplasty procedure, a femoral neck osteotomy is performed, wherein the neck of the femur is removed. Once the neck of the femur is removed, a femoral canal is created using an awl and/or a reamer. During the reaming procedure, the interior surfaces of the femoral canal become contaminated with loose debris.

The intermedullary brush attachment of FIG. 4 contains an elongated linear shaft 30 that defines an internal suction conduit 32. The suction conduit 32 is open at the tip 34 of the intermedullary brush attachment 16, thereby providing a passage for debris to pass into the suction conduit 32. Bulbous flanges 36, 38 are disposed on the brush shaft 30 at both the tip of the shaft 30 and at a point proximate the middle of the shaft 30. The purpose of the bulbous flanges 36, 38 is to limit the exposure of air and material to the entrance of the suction conduit 32, when the intermedullary brush attachment 16 is passed into a reamed femoral canal. By limiting the flow of air into the suction conduit 32, the degree of suction provided for the removal of debris directly in front of the mouth of the suction canal is improved.

Bristles 40, or some other flexible projections, radially extend from the brush shaft 30 in between the two bulbous flanges 36, 38. The brush bristles 40 extend to a diameter D, which is slightly larger than the internal diameter of the reamed femoral canal. As the intermedullary brush attachment 16 is introduced into the reamed femoral canal, the bristles 40 loosen debris from the interior surfaces. The loosened debris falls to the bottom of the femoral canal, wherein the debris is evacuated through the mouth of the suction conduit 24.

Referring back to FIG. 1, it can be seen that the acetabular brush attachment 18, the intermedullary brush attachment 16 and the general purpose suction head attachment 14 all share an identically configured base section 42. The base section 42 of all the suction head attachments 14, 16, 18 are adapted to be received by the handle element 12. Accordingly, the different suction head attachments 14, 16, 18 can be added to the handle element 12 or removed from the handle element 12 as is desired.

Figure 5:
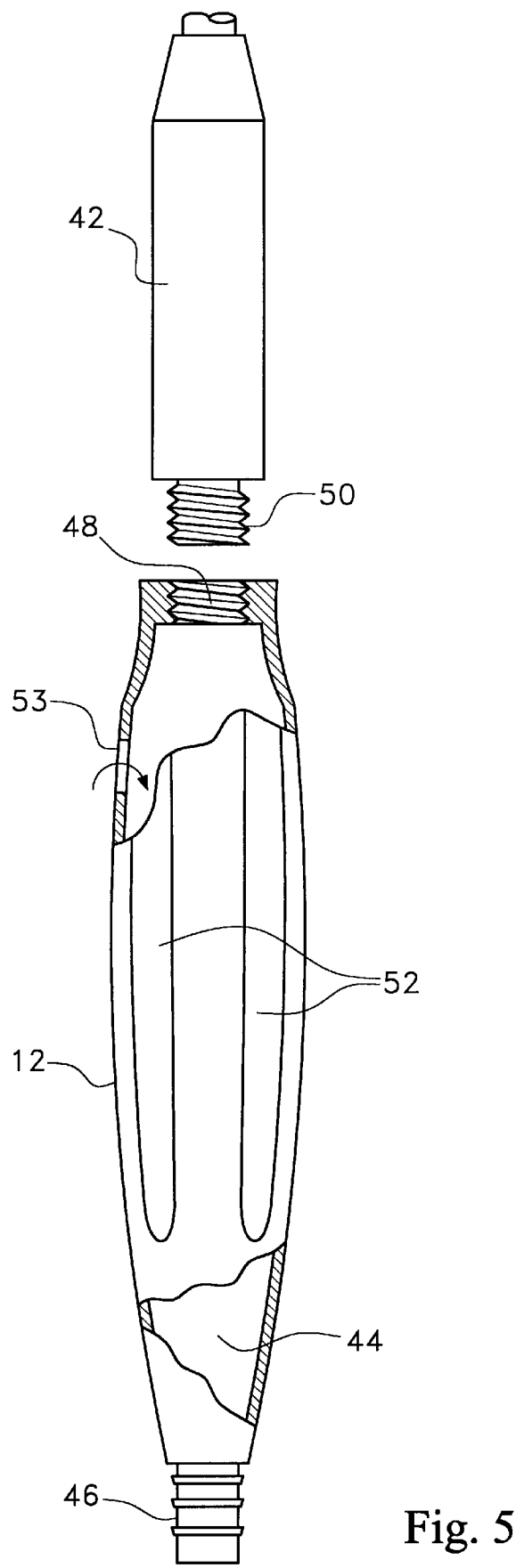
FIG. 5 is a fragmented side view of a handle element in accordance with the present invention.

Referring now to FIG. 5, it can be seen that the handle element 12 has two ends and defines a 44 conduit that extends through the handle element 12 between the two ends. A tube connector hub 46 is located at the first end of the handle element 12. The tube connector hub 46 connects to a suction tube (not shown) that leads to a medical waste collection basin within the operating room.

A pneumatic interconnect mechanism 48 is disposed at the second end of the handle element 12. In the shown embodiment, the pneumatic interconnect mechanism 48 is a female threaded coupling that is adapted to receive a male threaded coupling 50 that extends from the base 42 of the suction head attachments. Once the threaded male coupling is received by the pneumatic interconnect mechanism 48, the conduit 44 within the handle element 12 intercommunicates with the suction conduit within the suction head attachment, thereby providing suction to the suction head attachments.

In the prior art record, there are numerous different types of pneumatic interconnect mechanisms. Such mechanisms span from simple threaded couplings to complex quick-disconnect valves. Any such prior art pneumatic interconnect mechanism can be adapted for use in the present invention suction assembly and the present invention should not be considered limited to the one exemplary interconnect mechanism 48 shown.

The exterior of the handle element 12 is preferably contoured so that it can be firmly grasped and manipulated with a bloodied surgical glove. The shown embodiment contains fluting 52 on the exterior of the handle element 12. However, knurling and other contouring features may also be used. A vent aperture 53 may optionally be added to the handle element 12. The vent aperture 53 is a hole that extends into the handle element 12, thereby interconnecting the interior of the handle element 12 to the ambient air surrounding the handle element 12. If a vent aperture is present, a surgeon can place his/her finger over the vent aperture 53 and selectively control the degree of negative air pressure contained within the handle element 12. For example, if a surgeon completely covers the vent aperture 12, full suction will be experienced through the aperture(s) in the suction head attachment. If a surgeon either partially of fully uncovers the vent aperture 12, air will be sucked into the handle element through the vent aperture 12 and the suction experienced at the aperture(s) of the suction head will be proportionally less.

Returning to FIG. 1, it will be understood that in a total hip arthroplasty procedure, surgeons create a skin incision, dissect the soft tissue and dislocate the hip to be replaced. This initial surgical procedure can be done in one of many different ways. Such an initial surgical procedure does not require any special suction instruments. Accordingly, a surgeon may attach a general purpose suction head attachment 14 to the handle element 12 and use the suction assembly 10 in the same manner as he/she would use any prior art suction system.

After the hip joint is dislocated and exposed, a femoral neck osteotomy is performed and a femoral canal is created using a tapered awl and/or a reamer. Once the femoral canal is created, a surgeon alters the suction assembly 10 by removing the general purpose suction head attachment 14 and replacing it with the intermedullary brush attachment 16. Once the intermedullary brush attachment 16 is in place, the surgeon can use it to properly and quickly clean the femoral canal prior to the placement of a femoral prosthetic device into that canal.

After the femoral prosthetic device has been set into place, the surgeon can direct his/her attention to the acetabulum. First, the acetabular socket is reamed with a series of reamers until the reamed socket is at a desired size. Once the reaming procedure is complete, the acetabula socket must be cleaned. To clean the acetabular socket, the surgeon alters the suction assembly 10 by connecting the acetabular brush attachment 18 to the handle element 12. Once the acetabular brush attachment 18 is connected, it can be used to properly and quickly clean the acetabular socket prior to the placement of an acetabular cup into that socket.

Once the prosthetic devices are set in place, the surgeon closed the incision. Again, the surgeon may decide to alter the suction assembly 10 by placing a general purpose suction head attachment 14 onto the handle element 12.

By providing a single suction assembly that can be altered to the needs of a surgeon, a more efficient operation procedure can be maintained. The surgical team no longer has to waste time and energy connecting and disconnecting different suction devices to the limited number of suction tubes available in an operation room. Furthermore, by providing a suction system that provides suction heads specifically adapted to a specific surgical procedure, the required cleaning, sectioning and irrigating tasks can be performed in a more effective and rapid manner.

It will be understood that a person skilled in the art can make alternate embodiments of the present invention using functionally equivalent components that have not been specifically described. For example, alternate suction heads of different sizes and shapes can be used. All such modifications are intended to be included in the scope of this disclosure as defined by the appended claims.

What is claimed is:

1. A suction device for use in a surgical procedure, comprising:

a plurality of suction heads having a base segment, a tip segment and a suction conduit that extends through said base segment and said tip segment, wherein said base segment of each of said suction heads has a common configuration and wherein the tip section of a first suction head is configured as an acetabular brush, said acetabular brush includes a head section containing a generally hemispherically shaped surface, the tip section of a second suction head is configured as a intermedullary brush and the tip of a third suction head is configured as a suction instrument selected from a group consisting of Yankauer instruments, Poole instruments, Frazier instruments and sigmoidoscope instruments;

a single handle element having a first end, a second end, a coupling mechanism disposed at said second end, and a conduit that extends from said first end through said coupling mechanism at said second end, wherein said coupling mechanism is adapted to selectively engage said base segment of any of said plurality of suction heads and interconnects said conduit within said handle element with said suction conduit within that suction head.

2. The device according to claim 1, wherein a vacuum hose connector port is disposed at said first end of said handle element.

3. The device according to claim 1, wherein said acetabular brush includes a head section containing said generally hemispherically shaped surface having flexible protrusions extending outwardly therefrom.

4. The device according to claim 3, wherein said generally hemispherically shaped surface has an apex and an aperture is disposed at said apex that leads to said suction conduit.

5. The device according to claim 3, wherein a plurality of apertures are disposed in said generally hemispherically shaped surface, wherein each of said apertures leads to said suction conduit.

6. An acetabular brush, comprising:

a handle;

a shaft extending from said handle;

a head coupled to an end of said shaft opposite handle, wherein said head contains a generally hemispherically shaped surface; and flexible protrusions extending outwardly from said generally hemispherically shaped surface.

7. The brush according to claim 6, wherein said handle is selectively detachable from said shaft.

8. The brush according to claim 6, further including a conduit that extends through said handle, said shaft and into said head section, wherein at least one aperture is disposed in said generally hemispherically shaped surface that leads to said conduit.

9. The brush according to claim 8, wherein said generally hemispherically shaped surface has an apex and an aperture extends through said apex that leads to said conduit.

10. The brush according to claim 8, further including a suction hose connection coupled to said handle, wherein said suction hose connection leads into said conduit.

11. An intermedullary brush, comprising:

a shaft having a first end and a second end;

a handle connected to said first end of said shaft;

a plurality of flexible protrusions radially extending from at least one section of said shaft;

a first flange radially extending from said shaft proximate said second end and a second flange radially extending from said shaft at a predetermined point between said first end and said second end;

a conduit extending through said handle and said shaft, wherein said conduit is open at said second end of said shaft.

12. The brush according to claim 11, wherein said flexible protrusions extend from said shaft between said first flange and said second flange.

13. A suction assembly for use by a surgeon in a total hip replacement procedure, said assembly comprising:

an acetabular brush having a first suction conduit disposed therein; said acetabular brush includes a head section containing a generally hemispherically shaped surface, a intermedullary brush having a second suction conduit disposed therein;

a handle having a third suction conduit disposed therein, wherein said handle can be selectively coupled to either said acetabular brush or said intermedullary brush, whereby said third suction conduit selectively interconnects with either said first suction conduit or said second suction conduit, respectively.

14. The device according to claim 13, further including a suction instrument selectively connectable to said handle.

15. The device according to claim 14, wherein said suction instrument is selected from a group consisting of Yankauer instruments, Poole instruments, Frazier instruments and sigmoidoscopic instruments.

16. The device according to claim 13, wherein said acetabular brush includes:

a handle;

a shaft extending from said handle;

a head coupled to an end of said shaft opposite handle, wherein said head contains a generally hemispherically shaped surface; and flexible protrusions extending outwardly from said generally hemispherically shaped surface.

* * * * *